United States Patent [19]

Krieger, Jr.

[11] 4,010,640
[45] Mar. 8, 1977

[54] APPARATUS FOR MEASURING THE STIFFNESS CHARACTERISTIC OF STRUCTURAL ADHESIVES

[75] Inventor: Raymond Buchheimer Krieger, Jr., Abingdon, Md.

[73] Assignee: American Cyanamid Company, Stamford, Conn.

[22] Filed: Oct. 16, 1975

[21] Appl. No.: 622,913

[52] U.S. Cl. .......................... 73/150 A; 33/147 D; 336/30
[51] Int. Cl.² .................... G01N 19/04; G01B 7/24
[58] Field of Search ............... 73/150 R, 150 A; 33/147 D, 148 D; 336/30

[56] References Cited

UNITED STATES PATENTS

| 2,119,076 | 5/1938 | Dietrich | 33/148 D X |
| 2,543,429 | 2/1951 | Wood | 33/148 D X |
| 2,767,476 | 10/1956 | Strimel | 33/148 D |
| 3,577,775 | 5/1971 | Henderson | 73/150 A X |
| 3,608,365 | 9/1971 | Baucom et al. | 33/147 D X |

Primary Examiner—Herbert Goldstein
Assistant Examiner—John S. Appleman
Attorney, Agent, or Firm—Frank M. Van Riet

[57] ABSTRACT

An apparatus for measuring the stiffness characteristic of structural adhesives which encompasses a critically patterned series of sensor points which enables the recording of minute movements of a bonded specimen to which force is applied with exacting precision.

10 Claims, 9 Drawing Figures

APPARATUS FOR MEASURING THE STIFFNESS CHARACTERISTIC OF STRUCTURAL ADHESIVES

BACKGROUND OF THE INVENTION

The use of adhesives to bond materials to one another is becoming more and more wide-spread and, as a result, it is becoming more and more necessary to learn as much about each individual adhesive system in question when considering which to use for a particular service application. Skilled artisans are constantly searching for new and useful techniques which will enable them to choose one adhesive over another when confronted with a multitude of systems, each of which will apparently do the job.

One of the fields of exploration which has recently become of more concern to the artisan is in the area of stress analysis. The artisan must be able to predict the strength and durability of a particular adhesive system when considering its use. These features of adhesive systems have been very difficult to assess with any degree of particularity because commercially available devices with are designed to accumulate data of this sort have not proven accurate enough, not only from the standpoint of giving false or misleading information but from the standpoint of not being capable of detecting the minute movements involved when test samples are subjected to extraneous forces. Devices now in general use are subject to so many influencing factors that readings obtained therefrom are, in most instances, meaningless. Some of these influencing factors include (1) loading holes off center in producing specimen, (2) glue line voids off center in producing specimen, (3) glue line rotation during exertion of force on specimen, (4) adherend bending rotations of material when force exerted on specimen, (5) adherend tension differential of material during applications of force on specimen, (6) adherend shear deformation as force is exerted on specimen and the like. Each of these individual occurences are normally manifested during specimen tests and, consequently, each adds its influence to the final information received during the testing program. Other errors are introduced into the calculations by deficiencies inherent in the design of the texting apparatus, e.g., lever systems tend to include "slop" or play in the bearings or pivotal points thereof because lever ends move on arcs rather than in straight lines.

A complete and precise discussion of evaluation techniques and stress analysis for structural bonds under hostile environment can be found in an article in Adhasion, Vol. 18, No. 12, Dec. 1974, and continued in Vol. 19, No. 1, Jan. 1975, published by Bertelsmann Fachzeitschriften GmbH, said article having been authored by the instant inventor.

SUMMARY

I have now discovered a new and useful apparatus for obtaining stress data of adhesives so as to enable one to predict the strength and durability of that adhesive in a particular application. My new apparatus enables the stress analysis of structurally bonded components such as those useful in aircraft, missiles and space vehicles, so as to predict their strength, by obtaining a property of the adhesive called the shear stiffness, as described in the above articles.

My novel apparatus is not subject to errors produced by false strain signals from extraneous deformation of the test specimen, as discussed above, or from such errors as produce in lever systems which transform specimen strain to transformer core movement using bearings or pivot points which move on arcs rather than on straight lines. The instant apparatus overcomes these false signals because the sensor points that grip the specimen are arranged so that only the shear movement of the glue line can cause relative movement between the sensor points. Because the sensor points are close to the glue line and are preferably on a line through the center of gravity of the instrument, the instrument can rotate with small loads on the sensor points so they do not slip and cause error. Also the sensor point configuration minimizes error from tension strain. Since an instrument is mounted on each side of the test specimen, errors from eccentric or unsymetrical specimens are eliminated. Furthermore, strain motion is transferred by fixed end beam springs rather than other arc-related means so as to eliminate non-linear motion induced errors.

DESCRIPTION OF THE INVENTION INCLUDING PREFERRED EMBODIMENTS

As mentioned briefly above, the apparatus of the instant invention is used to measure the relative movement or displacement between two adhered materials as represented by the movement of sensor points in the device. The device uses a linear, variable, differential transformer to detect the specimen movement from the sensor points and transmits a signal through an amplifier to a recorder. Calculation, using the recorder information, enables one to obtain the relative shear strength of the adhesive and thereby predict its ultimate strength and durability.

Figure 1:
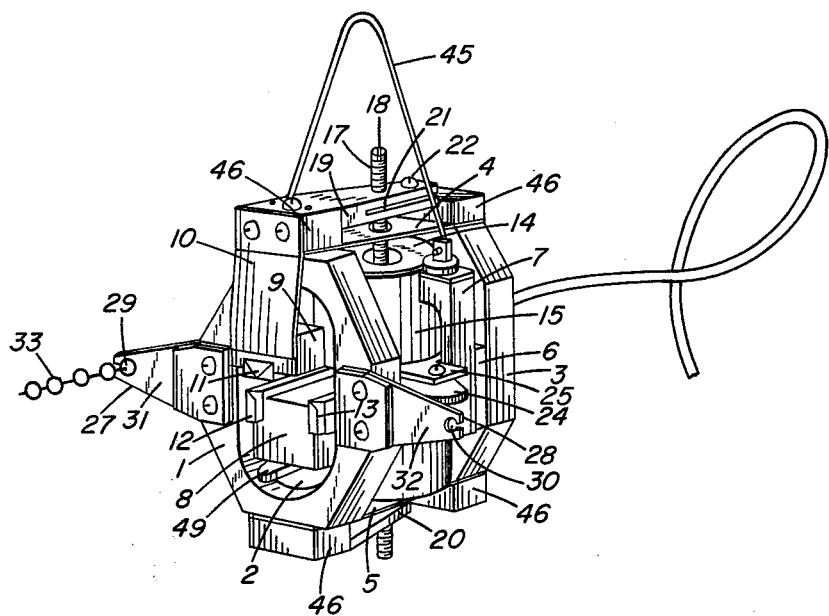
FIG. 1 is an isometric view of the complete extensometer of the instant invention.
Figure 2:
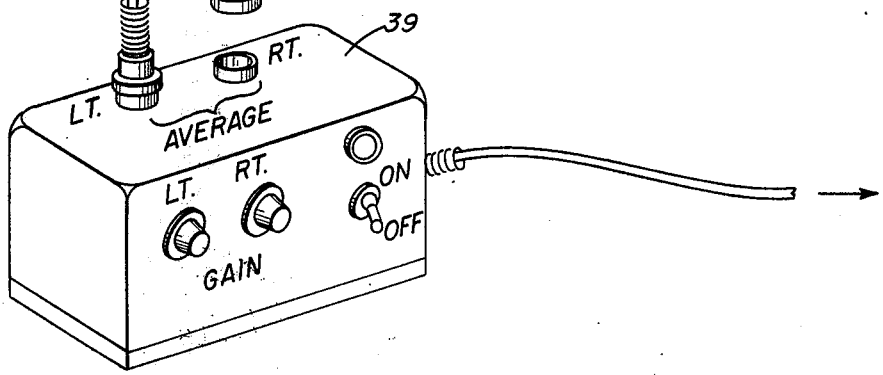
FIG. 2 is an isometric view of a pair of the instant instruments positioned on a bonded specimen preparatory to analysis thereof, showing the electronic hook-up thereof to an amplifier and recorder.
Figure 5:
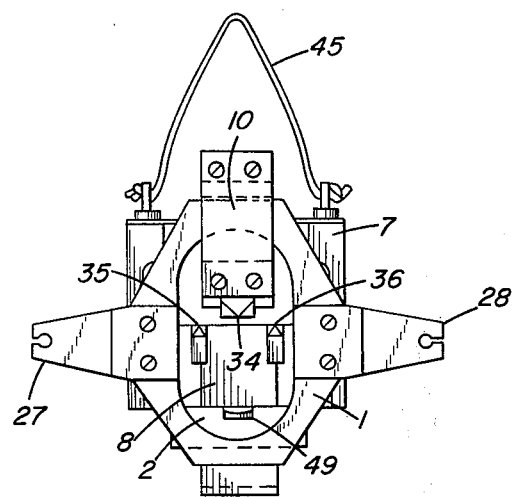
FIG. 5 is a schematic front view of the apparatus showing safety wire and mounting spring — sensor point positioning.

Referring now to FIG. 1, the device comprises a first frame 1 having an aperture 2 therein, more fully seen in FIG. 5. A second frame 3 constitutes the rear of the apparatus. Frame 3 can be of any desired configuration but should contain a conduit as seen in FIG. 2 for attaching a recording wire to the transformer. Plates 1 and 3 are connected at their upper sections by first plate spring 4 which is fully fixed, and at their lower sections by second plate spring 5 which is also fully fixed. By "fully fixed" is meant that the plate springs are so attached to the frames that no rotation about any of the three possible axis at their points of attachment is possible. The only allowable movement is up and down relative to the frames. Fixity bars 46 accomplish this result.

There is a supporting member 6 on second frame 3 which extends to frame 1, includes first mounting block 8 and movably fits into aperture 2. Second mounting block 9 is fixedly attached to third plate spring 10 which, in turn, is fixedly attached to frame 1, advantageously via fixety bar 46. A first sensor point 11 is fixedly mounted onto mounting block 9 within the confines of aperture 2. Third plate spring 10 conceivably could be attached directly to the face of frame 1. Second sensor point 12 and third sensor point 13 are fixedly mounted on mounting block 8 also within the confines of aperture 2. The positioning of these sensor points relative to one another and other parts of the device is set forth more fully hereinbelow. The sensor points are immovably mounted onto mounting blocks 8 and 9 so that they remain in place during the use of the instrument. The tips of sensor points 11, 12 and 13 must be sharp enough and hard enough to bit into the material from which the specimen being tested is made.

Figure 7:
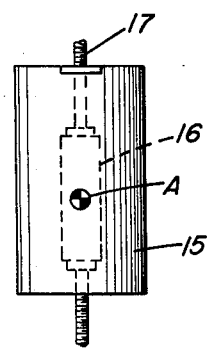
FIG. 7 is a view of the core positioning in the transformer of the apparatus.

Bracket means 7 is attached to supporting member 6 and is adapted to support the coil 14 of transformer 15 which is a linear, variable, differential transformer of known configuration comprising coil 14 and a core 16, best seen in FIG. 7. As can be seen, the transformer is positioned within the space formed by frames 1 and 3 and plate springs 4 and 5. Adjusting means 17 preferably comprises a threaded rod having a slot 18 at one end thereof which enables the rod to be turned with any suitable device such as a screwdriver. Rod 17 is threadably attached to the top and bottom of frame 1 via ears 19 and 20, respectively. Rod 17 passes through holes in plate springs 4 and 5 but does not touch either component. The core 16 of transformer 15 is attached to adjusting means 17, as seen in FIG. 7, and is positioned within the hollow region of the coil. As can be readily appreciated at this point in this discussion, since the coil of the transformer is attached to frame 3 through bracket 7 and supporting member 6 and the core of the transformer is attached to frame 1 through rod 17 and ears 19 and 20, the two transformer components are free to move with relation to one another when plate springs 4 and 5 are flexed. It is this configuration which enables the instant device to function.

The adjusting means 17 can be locked in place once the position of the core in the transformer has been adjusted via slot 18, by locking means 21 which comprises a slot in ear 19 and a screw 22. This device prevents accidental rotation of rod 17 once the instrument has been calibrated and mounted on the sample. Locking is effected by tightening screw 22 which causes the slot to be decreased because only the bottom section is threaded, see FIG. 4. It is important that once the core is located within the coil in the necessary position that it be retained at said position throughout the testing routine. The locking system accomplishes this. Techniques other than the slot and screw arrangement described above could be used for this purpose without departing from the scope of the instant invention. Once locked, the core cannot be in contact with the coil and the rod cannot be in contact with the spring plates as is true also when the locking means is not actuated and the instrument is being prepared for use by adjusting means 17.

Figure 4:
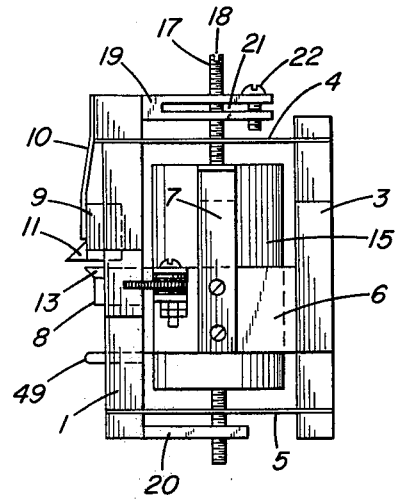
FIG. 4 is a side schematic view of the instrument.
Figure 6:
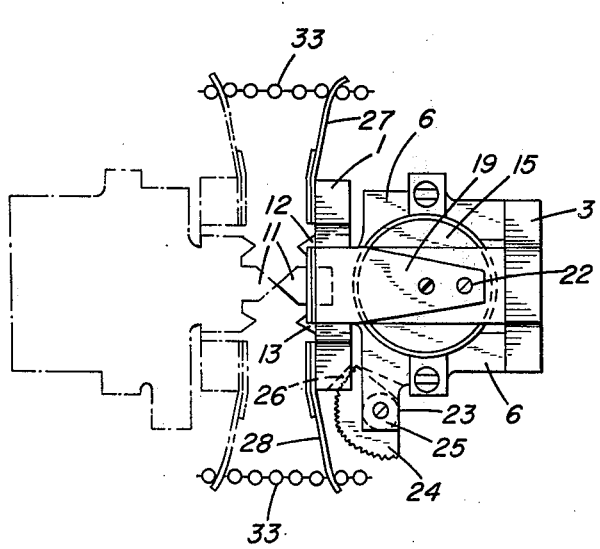
FIG. 6 is a top schematic view showing a pair of instruments mounted on a sample with one instrument in phantom.

The frames 1 and 3 are also locked in position while the instrument is being stored or while it is being mounted upon the specimen to be tested. Any means can be used whereby the plate springs 4 and 5 are prevented from flexing, either by contacting the spring plates per se or by rigidifying the frames. I have found the latter to be more readily accomplished and therefore preferred. Reference to FIGS. 4 and 6 will best serve to show a useful locking system. Locking means 23 comprises knurled member 24 which rotates on projection 25 of supporting member 6 and fits snugly into slot 26 in frame 1 thereby rigidifying the entire instrument. Other locking means could also be used.

Again referring to FIG. 1, mounting plate springs 27 and 28 have orifices 29 and 30 therein. The springs 27 and 28 are affixed at their ends to both sides of frame 1. They may be fixedly or pivotally attached thereto. The ends 31 and 32 of mounting plate springs 27 and 28 extend beyond the vertical edges of frame 1 and are adapted to receive means for attaching two instruments together. The attaching means 33 can constitute such systems as a ball chain, as is shown, a pair of interlocking hooks, a hook and eye and the like. The mounting plate springs 27 and 28 are generally made of a tension or ductile metal such as titanium and serve, along with the attaching means 33, to secure the instrument in position on the specimen being tested. The tension of these springs can be varied such as by adding a leaf to the spring, as shown.

It is critical that mounting plate springs 27 and 28 are attached to frame 1 and not frame 3 in order to prevent plate springs 4 and 5 from buckling when the instrument is being used. As shown in the drawings, the mounting plate springs cause tension on plate springs 4 and 5 which is required. If the mounting plate springs were attached to frame 3, however, engaging means 33 would compress plate springs 4 and 5 and cause then to buckle, thereby causing an error in the signal.

As mentioned above, the positioning of mounting plate springs 27 and 28, in relation to sensor points 11, 12 and 13 are important. I have found that for proper operation of the instrument, mounting plate springs 27 and 28 should be positioned such that they are affixed to frame 1 substantially within a horizontal plane running through the center of gravity of the apparatus. In this manner, mounting plate springs 27 and 28 enable all three sensor points to be held securely against the surfaces of the specimen to be tested and retain the instrument's position on the specimen.

Figure 9:
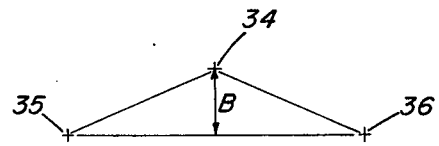
FIG. 9 is a view of the triangle formed by drawing an imaginary line connecting the tips of the sensor points.

Sensor points 11, 12 and 13 are also positioned in a manner critical to the operability of the instant apparatus. They are positioned such that sensor points 12 and 13 are in the same horizontal plane with respect to frame 1, sensor point 11 is positioned above sensor points 12 and 13 and moves pivotally around an imaginary line drawn parallel to sensor points 12 and 13 and the tips of sensor points 12 and 13 are in substantially the same perpendicular plane, i.e., tips 35 and 36 must be touching the same perpendicular plane. Reference to FIGS. 5 and 9 clarifies the sensor point positioning and also clearly indicates how the sensor points are attached to frames 1 and 3. Sensor point 11 is affixed to frame 1 through mounting block 9 and spring 10. It is free to move as described above. Sensor points 12 and 13 are affixed to frame 3 via mounting block 8 and means 6. Sensor points 12 and 13 are preferably on a line through the center of gravity of the apparatus shown at point A, FIG. 7. An imaginary line drawn between the tips 34, 35 and 36 forms a triangle. The triangle is preferably isoceles as shown in FIG. 9 wherein sensor point tip 34 is positioned on an imaginary perpendicular line bisecting an imaginary line connecting sensor point tips 35 and 36. The height of the triangle, i.e., that area between tip 34 and the line between tips 35 and 36 should be as small as possible in order to obtain the best results, i.e., distance B at FIG. 9.

Figure 3:
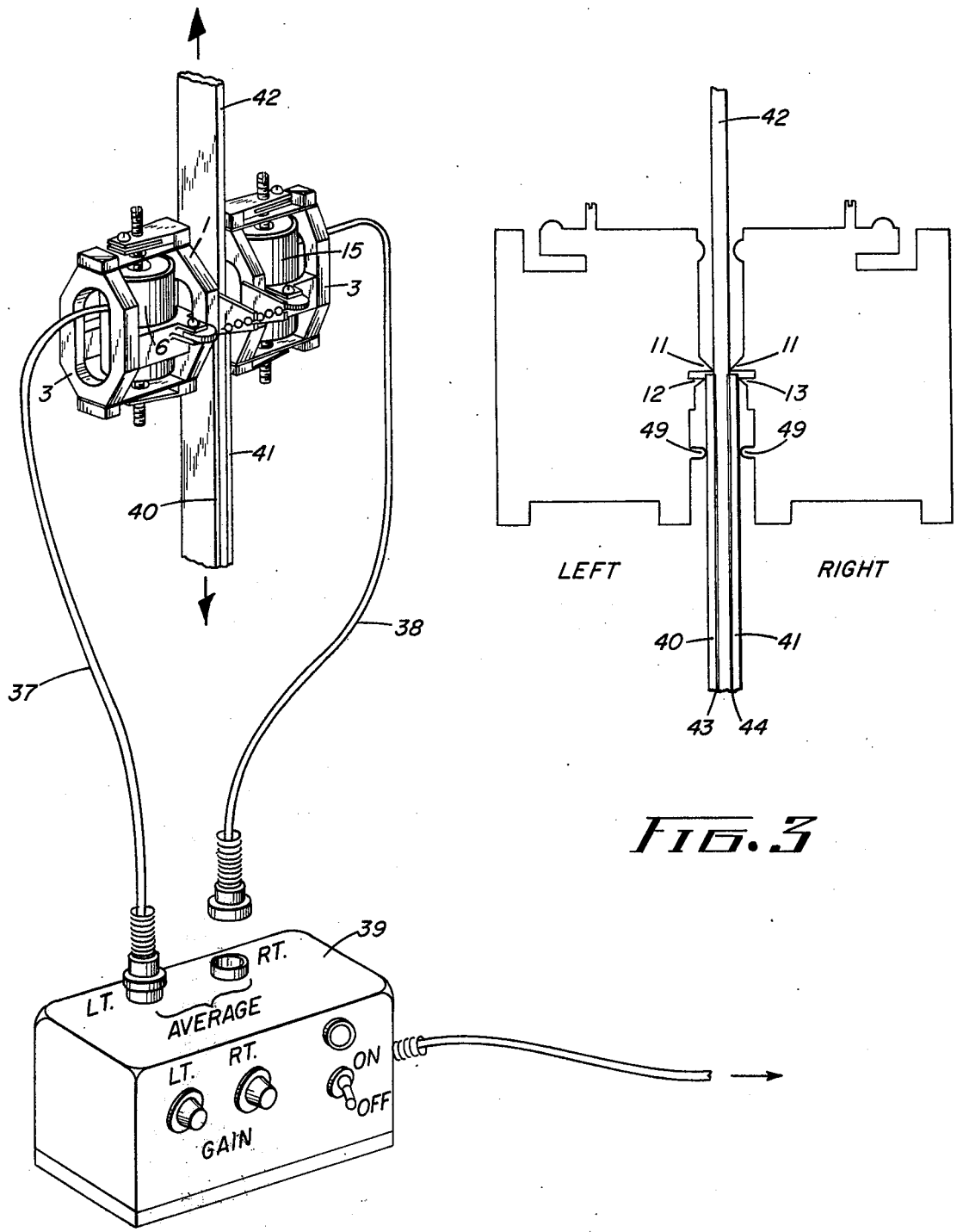
FIG. 3 is a phantom view of a pair of apparatuses as mounted on a test specimen as in FIG. 2.

In operation, the instruments are first adjusted by attaching wires 37 and 38, see FIG. 2, to an amplifier 39 which, in turn, is hooked up to a recorder. Locking means 23 is then engaged so as to lock frames 1 and 3. Screw 22 is loosened to unlock means 21 and the core 16 is adjusted within transformer 15 to its proper position which is determined by a zero voltage signal to the recorder. Means 21 is then set by tightening screw 22 and the instruments are then mounted on the test specimen to measure the shear strength of the adhesive, see FIG. 2, a phantom view of which is shown in FIG. 3. As is readily seen, three material sheets 40, 41 and 42 are adhered to one another via glue lines 43 and 44. The specimen has been manufactured such that no glue is applied to the upper portion of sheet 42. The instruments are mounted on the specimen as shown in FIG. 3 with sensor point 11 of each apparatus biting into sheet 42, and sensor points 12 and 13 of each apparatus biting into sheets 40 and 41 and nodule 49 maintaining the instruments's balance. Nodule 49 is preferably in the same perpendicular plane as tips 35 and 36. It is preferred that all the sensor points be as close as possible to the point where sheets 40 and 41 and the glue lines end. Attaching means 33, which are preferably of equal length, are then engaged to their opposite mounting plate springs to thereby suspend the instruments from the specimen. Safety wire 45 can be used, if desired, to prevent damage to the instruments if means 33 fails. The frames are then unlocked and the instruments are ready for use. Although the above description specified that the core adjustment should be accomplished before the instruments are mounted on the test specimen, said adjustment of the core could be carried out after mounting the instruments. However, such is not preferred. As can be readily appreciated, since spring 10 enables sensor point 11 to move, it comes into contact with sheet 42 regardless of the thickness of sheets 40 and 41.

Force is then applied to the test specimen as shown by the arrows in FIG. 2. As the force increases, the specimen sheets 40, 41 and 42 begin to move very minutely. Since sensor points 11, 12 and 13 are tenaciously gripping the sheets, they also move. The movement of the sensor points creates a movement in the core of the transformer in relation to the coil and consequently a signal is emitted through wires 37 and 38 and amplifier 39 and are recorded on the recorder.

Figure 8:
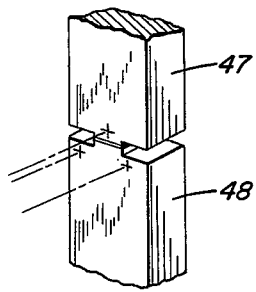
FIG. 8 is an isometric view of a second type of sample useful with the instant apparatus and the positioning of the sensor points thereon.

Another form of test specimen which can be used with the instant apparatus to test the tension strength of the adhesive is shown in FIG. 8. Here, two materials 47 and 48 are adhered together at their butt ends. The apparatuses are mounted thereon with the tips of the sensor points positioned as marked +. Force applied to the specimen as discussed above, results in a movement of the materials and consequently a recording of said movement.

The instruments are calibrated prior to their use on an actual test specimen. For example, using the specimen of FIG. 3, if a dummy specimen is composed of two well lubricated plastic sheets sandwiched between three clamped metal sheets, the instruments are mounted on the dummy specimen as described above and the metal sheets are then moved a known distance using a calibrated device, the signal again passes to the recorder and, as a result, a record is made of a known deviation in the specimen. Comparison to that recorded movement of the actual specimen results in data which is used to calculate the shear stiffness of the adhesive.

As discussed briefly above, use of the instant apparatus eliminates most of the errors which are common to previously used devices and those which are not eliminated can be compensated for. Specifically, where the specimen is incorrectly fabricated, e.g., the loading holes are off center or the glue line voids are off center, the matching of the signals emitted by both the left and right instruments enables one to either average them out if the difference between them is minor or discard the sample if the difference in gross. Existing devices cannot even detect that the specimen is defective.

When the glue line rotates during the distortion of the specimen, the instant apparatus still emits a valid signal because it is only supported on sensor points 11, 12 and 13 which are at or near the center of gravity. The rotation does not cause an error as with existing devices which are clamped to the specimen.

In the type of error normally produced by adherend tension differential and adherend shear deformation distortions, since stretching of the specimen is tolerated as long as sensor points 12 and 13 are solid and do not move, these errors can be calculated and thereafter substracted from the first readings obtained. It can therefore be readily appreciated that the most commonly troublesome errors in adhesion bond analysis have been effectively eliminated by the instant apparatus and that more meaningful data can therefore be obtained therefrom.

I claim:

1. An apparatus adapted to be used in conjunction with a second apparatus having the same structure but of a mirror image configuration for the measurement of the shear stiffness characteristic of structural adhesives so as to enable the accurate stress analysis of an adhesive bond comprising
  A. a first frame having an aperture therein,
  B. a second frame,
  C. a first plate spring fully fixed at one of its ends to the upper section of said first frame and at the other of its ends to the upper section of said second frame,
  D. a second plate spring fully fixed at one of its ends to the lower section of said first frame and at the other of its ends to the lower section of said second frame,
  E. a first supporting member on said second frame extending movably into said aperture,
  F. a second supporting member on said first frame comprising a third spring which is positioned above said first supporting member, pivotably rotates on an axis and is adjacent said aperture,
  G. a first sensor point fixedly mounted on said second supporting member within the confines of said aperture,
  H. second and third sensor points fixedly mounted on said first supporting member within the confines of said aperture,
  I. bracket means attached to said second frame, J. adjusting means attached to the top and bottom of said first frame,
K. a linear, variable, differential transformer comprising a coil and a core, the coil of which is supported by said bracket means and positioned within the space between said first and second frames and the core of which is affixed to said adjusting means and positioned within the hollow of said coil,
L. first locking means adjacent said adjusting means and adapted to prevent accidental movement thereof,
M. interactive, second locking means positioned adjacent to said first and second frames and adapted, when engaged, to minimize flexing of said first and second plate springs,
N. mounting plate spring means affixed to the first frame at its middle, extending beyond the vertical edges of said first frame and having attaching means within the extending portions thereof,
said sensor points being positioned such that said first point is above said second and third points and moves pivotably around an imaginary line drawn parallel to said second and third sensor points, said second and third points are in the same horizontal plane with respect to said first frame, and the tips thereof touch substantially the same vertical plane.

2. An apparatus according to claim 1 wherein said adjusting means comprises a threaded rod.

3. An apparatus according to claim 1 wherein an ear is affixed to both the top and bottom of said first frame and said adjusting means is threadably engaged therewith.

4. An apparatus according to claim 1 wherein electrically conductive wire is attached to said transformer and is adapted to connect to an amplifier.

5. An apparatus according to claim 4 wherein said wire is connected to an amplifier and said amplifier is connected to a recording device.

6. An apparatus according to claim 1 wherein said second and third sensor points are on a line through the center of gravity of the apparatus.

7. An apparatus according to claim 1 wherein an imaginary line drawn between the tips of said first, second and third sensors forms a triangle.

8. An apparatus according to claim 7 wherein said first sensor point is positioned on an imaginary perpendicular line bisecting an imaginary line connecting said second and third sensor points.

9. An apparatus according to claim 1 wherein a stabilizing nodule is attached to said first supporting member and below said second and third sensor points.

10. A method for measuring the shear stiffness characteristic of a structural adhesive comprising
 a. attaching a pair of apparatuses as defined in claim 1, one to each side of a sample comprising two outer pieces of material adhered to the opposite sides of a third piece of material with said first sensor point of each apparatus being in contact with said third piece and said second and third sensor points of each apparatus being in contact with an outer piece, said apparatuses being attached together through their mounting plate springs,
 b. applying an external force to said sample,
 c. recording the movement of said pieces as a result of said force by amplifying the voltage emitted by said transformer and
 d. transposing said recordings into information indicative of the relative strength of said adhesive bond.

* * * * *